United States Patent
Lindmark et al.

(10) Patent No.: US 10,682,353 B2
(45) Date of Patent: Jun. 16, 2020

(54) VARLITINIB FOR USE IN THE TREATMENT OF RESISTANT OR REFRACTORY CANCER

(71) Applicant: ASLAN Pharmaceuticals PTE LTD, Singapore (SG)

(72) Inventors: Bertil Lindmark, Singapore (SG); Lisa Ooi, Singapore (SG)

(73) Assignee: ASLAN Pharmaceuticals PTE LTD, Singapore (SG)

( * ) Notice: Subject to any disclaimer, the term of this patent is extended or adjusted under 35 U.S.C. 154(b) by 0 days.

(21) Appl. No.: 15/757,189

(22) PCT Filed: Sep. 5, 2016

(86) PCT No.: PCT/EP2016/070893
§ 371 (c)(1),
(2) Date: Mar. 2, 2018

(87) PCT Pub. No.: WO2017/037300
PCT Pub. Date: Mar. 9, 2017

(65) Prior Publication Data
US 2018/0243302 A1    Aug. 30, 2018

Related U.S. Application Data

(60) Provisional application No. 62/217,332, filed on Sep. 11, 2015, provisional application No. 62/217,346, filed on Sep. 11, 2015.

(30) Foreign Application Priority Data

Sep. 4, 2015 (GB) .................................... 1515712.6
Sep. 4, 2015 (GB) .................................... 1515714.2
(Continued)

(51) Int. Cl.
*A61K 31/517* (2006.01)
*C07D 239/94* (2006.01)
(Continued)

(52) U.S. Cl.
CPC .......... *A61K 31/517* (2013.01); *A61K 9/0053* (2013.01); *A61K 31/51* (2013.01);
(Continued)

(58) Field of Classification Search
CPC .............................. A61K 31/517; A61P 35/00
(Continued)

(56) References Cited

U.S. PATENT DOCUMENTS 7,452,895 B2 * 11/2008 Wallace ................ C04B 35/632
514/266.2
10,357,494 B2    7/2019 Lindmark et al.
(Continued)

FOREIGN PATENT DOCUMENTS

EP      2 963 114 A1    1/2016
WO   2005/016346 A1    2/2005
(Continued)

OTHER PUBLICATIONS www.asianscientist.com Aslan Pharmaceuticals press release, Aug. 19, 2015. https://www.asianscientist.com/2015/08/pharma/aslan-varlitinib-cholangiocarcinoma/ (Year: 2015).*
(Continued)

*Primary Examiner* — Craig D Ricci
*Assistant Examiner* — Janet L. Coppins
(74) *Attorney, Agent, or Firm* — Prismatic Law Group, PLLC

(57) ABSTRACT

The present disclosure provides a method of treating a patient with refractory or resistant cancer by administering a therapeutically effective amount of a compound of formula (I), such as Varlitinib, or an enantiomer thereof or a pharmaceutically acceptable salt of any one of the same. Also provided is a compound of formula (I) for use in the treatment of resistant or refractory cancer and use of a
(Continued)

compound of formula (I) for the manufacture of a medicament for the treatment of resistant or refractory cancer.

14 Claims, 2 Drawing Sheets

(30) Foreign Application Priority Data

| Sep. 4, 2015 | (GB) | 1515716.7 |
|---|---|---|
| Sep. 4, 2015 | (GB) | 1515718.3 |
| Apr. 1, 2016 | (GB) | 1605583.2 |
| May 17, 2016 | (GB) | 1608660.5 |

(51) Int. Cl.

| A61K 31/51 | (2006.01) |
|---|---|
| A61P 35/00 | (2006.01) |
| A61K 9/00 | (2006.01) |
| A61K 31/7068 | (2006.01) |
| A61K 33/24 | (2019.01) |
| A61K 31/282 | (2006.01) |
| A61K 31/513 | (2006.01) |

(52) U.S. Cl.
CPC .......... *A61K 31/7068* (2013.01); *A61K 33/24* (2013.01); *A61P 35/00* (2018.01); *C07D 239/94* (2013.01); *A61K 31/282* (2013.01); *A61K 31/513* (2013.01); *A61K 2300/00* (2013.01)

(58) Field of Classification Search
USPC .......................................................... 424/649
See application file for complete search history.

(56) References Cited

U.S. PATENT DOCUMENTS

| 2015/0086541 A1 | 3/2015 | Aguilar-Cordova |
|---|---|---|
| 2018/0243302 A1 | 8/2018 | Lindmark et al. |
| 2018/0256578 A1 | 9/2018 | Lindmark et al. |
| 2018/0353510 A1 | 12/2018 | Lindmark et al. |
| 2019/0117655 A1 | 4/2019 | Lindmark et al. |
| 2019/0134034 A1 | 5/2019 | Ooi et al. |
| 2019/0321365 A1 | 10/2019 | Lindmark |
| 2020/0009144 A1 | 1/2020 | Lindmark et al. |

FOREIGN PATENT DOCUMENTS

| WO | 2008/094484 A2 | 8/2008 |
|---|---|---|
| WO | 2008/122779 A1 | 10/2008 |
| WO | 2010/127417 A2 | 11/2010 |
| WO | 2013/112942 A1 | 8/2013 |
| WO | 2014/022138 A2 | 2/2014 |
| WO | 2015/027915 A1 | 3/2015 |
| WO | 2015/061752 A1 | 4/2015 |
| WO | 2015/153514 A1 | 10/2015 |
| WO | 2016/065330 A1 | 4/2016 |
| WO | 2017/037292 A1 | 3/2017 |
| WO | 2017/037298 A1 | 3/2017 |
| WO | 2017/037299 A1 | 3/2017 |
| WO | 2017/037300 A1 | 3/2017 |
| WO | 2017/184086 A1 | 10/2017 |
| WO | 2017/223275 A1 | 12/2017 |
| WO | 2018/004465 A1 | 1/2018 |
| WO | 2019/083455 A1 | 5/2019 |
| WO | 2019/083456 A1 | 5/2019 |
| WO | 2019/083457 A1 | 5/2019 |
| WO | 2019/083458 A1 | 5/2019 |

OTHER PUBLICATIONS

Zhang et al, Hepatology (2010), pp. 975-986. (Year: 2010).*
Wang et al, J. Cellular Biochemistry (2014), vol. 115 (8), pp. 1381-1391. (Year: 2014).*
Ellard et al., Abstract #3603: ARRY-334543 in ErbB2 positive metastatic breast cancer and other ErbB expressing-cancers: experience from expansion cohorts on a phase I study, American Association of Cancer Research, AACR Annual Meeting, Apr. 18-22, 2009, Denver, CO, 3 pages.
International Search Report and Written Opinion, International Application No. PCT/EP2016/070893 (published as WO 2017/037300), dated Dec. 14, 2016, 8 pages.
Kim et al., 664P: Phase IIA study to evaluate the biological activity of ASLAN001 in HER-1/2 co-expressing or HER-2 amplified advanced gastric cancer, Annals of Oncology, vol. 25, No. Supp 4, p. iv226 (2014).
Varlitinib, Database PubChem Compound, NCBI Database accession No. 42642648, Jul. 20, 2009.
Wang et al., ARRY-334543 Reverses Multidrug Resistance by Antagonizing the Activity of ATP-Binding Cassette Subfamily G Member 2, Journal of Cellular Biochemistry, vol. 115, No. 8, pp. 1381-1391 (Aug. 2014).
Anonymous, "ASLAN Pharmaceuticals receives orphan drug designation from FDA for ASLAN001 (varlitinib) in cholangiocarcinoma," Aslan Pharmaceuticals, Aug. 13, 2015.
Anonymous, "ASLAN pharmaceuticals reports positive top-line results for phase 2 clinical trial of varlitinib in metastatic breast cancer-second-line treatment with varlitinib demonstrated significant tumour shrinkage in HER2-postiive breast aancer patients," Aslan Pharmaceuticals, Feb. 9, 2017.
Asian Scientist, "ASLAN's Bile duct cancer drug given FDA orphan drug status," Aug. 19, 2015.
Array Biopharma, Dr. Eli Wallace, "Selective inhibitors of the ErbB-family of receptor tyrosine kinase," Apr. 2, 2011.
Ooi et al, "Varlitinib demonstrates potent antitumor efficacy in patient-derived gastric cancer xenograft models," Proceedings of the American Association for Cancer Research 107th annual meeting, Cancer research, Apr. 20, 2016, vol. 76, No. 14 (supp), Abstract No. 4719.
Myers, "Array Biopharma's ARRY-543 shows potential clinical benefit in cancer patients," Apr. 23, 2009, FierceBiotech.
Blackwell et al, "Pan-ErbB inhibition by ARRY-334543 is superior to selective ErbB inhibition in a preclinical model that signals through multiple ErbB receptors," Proceedings of the American Association for Cancer Research Annual Meeting 101st meeting, Cancer Research, Apr. 21, 2010, vol. 70, No. 8 (supp), Abstract No. 3610.
Bushey, "ASLAN pharmaceuticals gains orphan designation for rare cancer drug," Rdmag, available at https://www.rdmag.com/news/2015/08/aslan-pharmaceuticals-gains-orphan-designation-rare-cancer-drug, Aug. 19, 2015.
Anderson et al, "In vivo activity of ARRY-334543, a potent, small molecule inhibitor of EGFR/ErbB2 in combination with trastuzumab or docetaxel," Proceedings of the American Association for Cancer Research Annual Meeting, Cancer Research, Apr. 18 to 22, 2009.
Deng et al, "Chemotherapy and target therapy for hepatocellular carcinoma: New advances and challenges," World Journal of Hepatology, Apr. 18, 2015, vol. 7, No. 5, 787-798.
Ellard et al, "Abstract #3603: ARRY-334543 in ErbB2 positive metastatic breast cancer and other ErbB expressing cancers: experience from expansion cohorts on a phase 1 study," Proceedings of the American Association for Cancer Research Annual Meeting, Cancer Research, Apr. 18 to 22, 2009.
Hirsch et al, "Epidermal growth factor receptor inhibition in lung cancer: status 2012," Journal of Thoracic Oncology, Mar. 1, 2013, vol. 8, No. 3, 373-384.
Jänne et al, "Phase I dose-escalation study of the pan-HER inhibitor, PF299804, in patients with advanced malignant solid tumors," Clinical cancer research, Mar. 1, 2011, vol. 17, No. 5, 1131-1139.
Kim et al, "664P: Phase IIa study to evaluate the biological activity of ASLAN001 in HER-1/2 co-expressing or HER-2 amplified advanced gastric cancer," Annals of Oncology, vol. 25, Sup 4, 2014, iv226.
Database PubChem accession No. 42642648, Varlitinib, created Jul. 20, 2009, modified Dec. 3, 2016.

(56) References Cited

OTHER PUBLICATIONS

Lee et al, "In vivo activity of ARRY-543, a potent, small molecule inhibitor of EGFR/ErbB-2 in combination with trastuzumab or docetaxel," Cancer Research, vol. 69, No. 2, suppl. S, Jan. 2009, 200s.

Nam et al, "The irreversible pan-HER inhibitor PF00299804 alone or combined with gemcitabine has an antitumor effect in biliary tract cancer cell lines," Investigational New Drugs, Dec. 25, 2011, vol. 30, No. 6, 2148-2160.

Nehls et al, "Capecitabine plus oxaliplatin as first-line treatment in patients with advanced biliary system adenocarcinoma: a prospective multicentre phase II trial," British Journal of Cancer, vol. 98, No. 2, Jan. 8, 2008, 309-315.

Rothenberg et al, "A Phase I study of ARRY-543, a potent, selective reversible inhibitor of ErbB receptors," International Conference: Molecular Targets and Cancer Therapeutics, Oct. 26, 2007, Abstract No. B257.

Shuen et al, "Varlitinib demonstrates tumor regression and vessel normalisation in ErbB-dependent and mutated beta-catenin hepatocellular carcinoma patient-derived xenograft model," Cancer research, vol. 78, No. 13, supplement 1, Jul. 1, 2018.

Wang et al, "ARRY-334543 reverses multidrug resistance by antagonizing the activity of ATP-binding cassette subfamily G member," Journal of Cellular Biochemistry, Aug. 2014, vol. 115, No. 8, 1381-1391.

Wang et al, "The potential of panHER inhibition in cancer," Frontiers in Oncology, Jan. 28, 2015, vol. 5, article 2, 1-12.

Zhang et al, "Preclinical assessment of simultaneous targeting of epidermal growth factor receptor (ERBB1) and ERBB2 as a strategy for cholangiocarcinoma therapy", Hepatology, Sep. 2010, vol. 52, No. 3, 975-986.

* cited by examiner

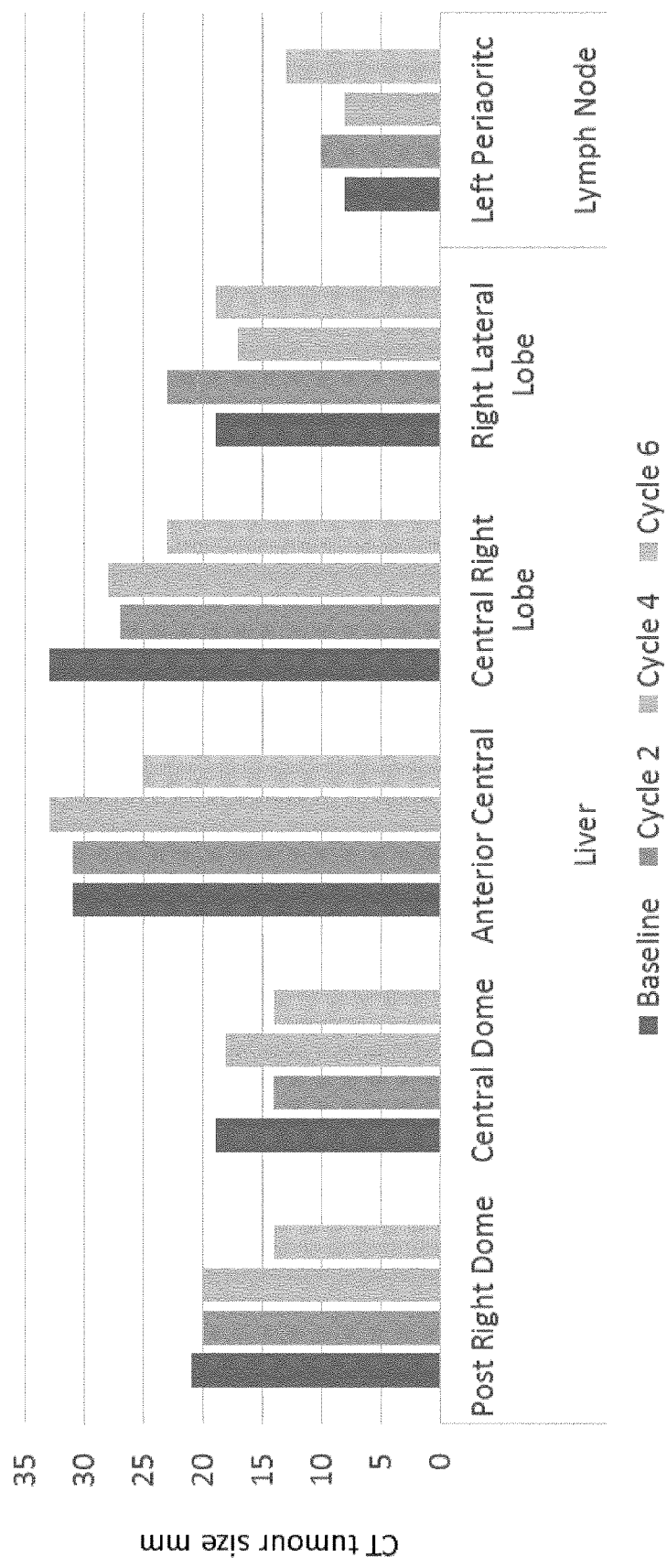
Figure 1  Varlitinib 400mg bi-daily as a Monotherapy

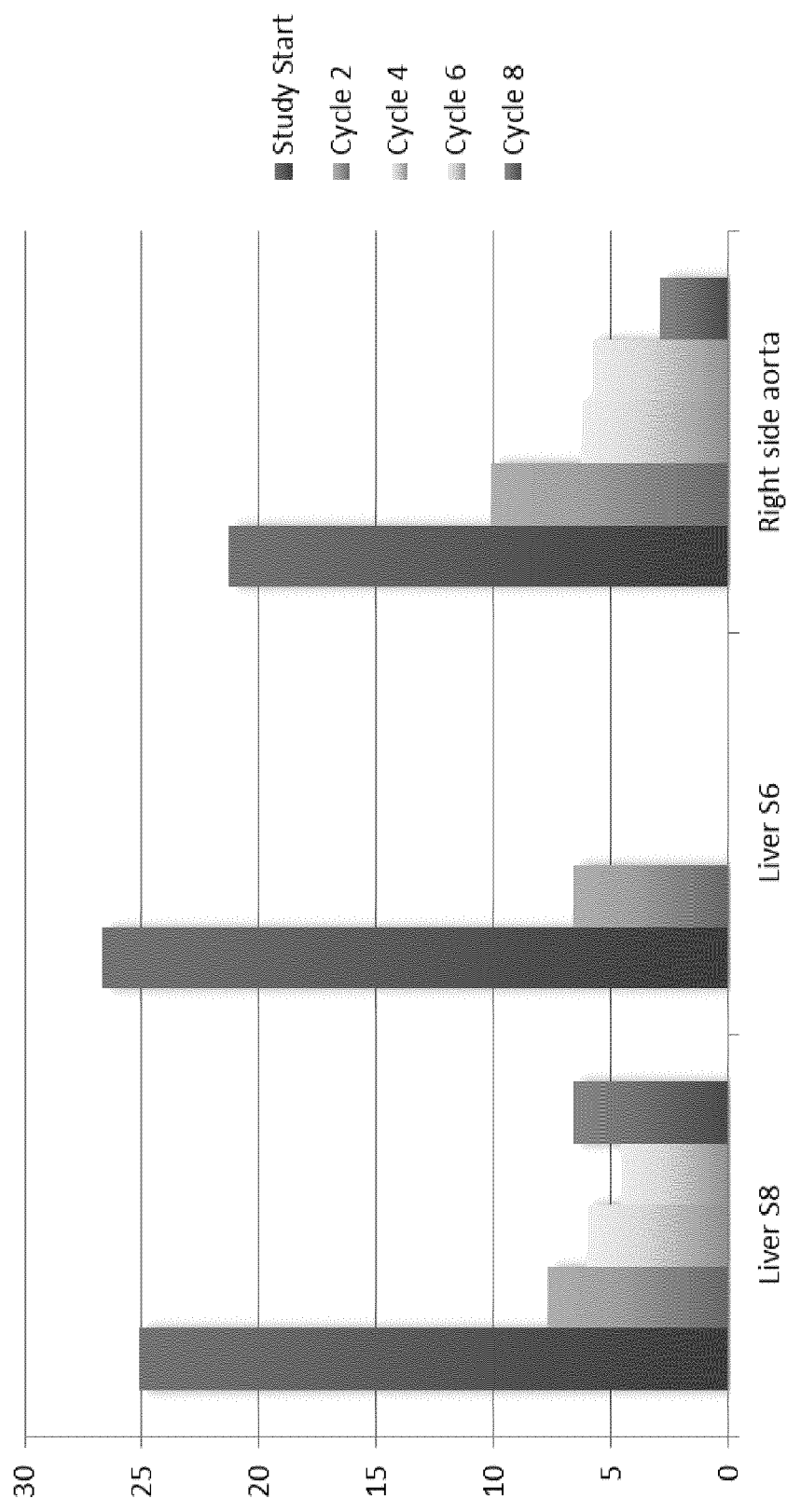
Figure 2  Varlitinib 400mg Bi-daily in combination with chemotherapy

VARLITINIB FOR USE IN THE TREATMENT OF RESISTANT OR REFRACTORY CANCER

CROSS-REFERENCE TO RELATED APPLICATIONS

This application is a 371 national phase of International Patent Application No. PCT/EP2016/070893 filed Sep. 5, 2016, which claims priority to British Patent Application No. 1515712.6 filed Sep. 4, 2015, British Patent Application No. 1515714.2 filed Sep. 4, 2015, British Patent Application No. 1515716.7 filed Sep. 4, 2015, British Patent Application No. 1515718.3 filed Sep. 4, 2015, U.S. Patent Application No. 62/217,332 filed Sep. 11, 2015, U.S. Patent Application No. 62/217,346 filed Sep. 11, 2015, British Application No. 1605583.2 filed Apr. 1, 2016, and British Patent Application No. 1608660.5 filed May 17, 2016, the content of each of which applications is incorporated herein by reference.

The present disclosure relates to a therapy comprising a type I tyrosine kinase inhibitor for the treatment of refractory or resistant cancers. The present disclosure also relates to a new patient population.

BACKGROUND

There are many cancers that are difficult to treat and although therapy is available, there appears to exist or to come into existence, a degree of resistance to the therapy. Primary resistance may occur in that cancer is not responsive to treatment from the outset. Secondary or acquired resistance also occurs quite frequently, which means that a therapy to which the patient seems to respond, at a certain time, loses its efficacy.

There are numerous reasons for resistance, for example some cancers are discovered at a late stage and/or a simply not responsive to treatment.

Mechanisms by which cancers avoid the therapeutic effect include but are not limited to:
i) mutations which render the cancer less vulnerable to the treatment (eg mutation of the site of action of the therapy),
ii) active transportation of the drug out of the tumor, for example by p-glycolation,
iii) building up physical defences, for example stroma which inhibit certain immune responses, and
iv) certain cancers develop paths to repair damage caused by some anti-cancer therapies.

Tumor heterogeneity may also contribute to resistance, where small subpopulations of cells may acquire or stochastically already possess some of the features enabling them to emerge under selective drug pressure. This is a problem that many patients with cancer encounter, and it obviously limits the therapeutic alternatives that are effective and worsens the prognosis.

Thus based on tumor response to the initial therapy, cancer resistance can be broadly classified into two categories, primary and acquired (Meads et al., 2009; Lippert et al., 2011). While primary drug resistance exists prior to any given treatment, acquired resistance occurs after initial therapy. Unfortunately, the majority of patients will likely develop resistance at a certain point of treatment.

Thus there a huge clinical need for improved therapies to address this unmet patient need.

(R)—N4-[3-Chloro-4-(thiazol-2-ylmethoxy)-phenyl]-N6-(4-methyl-4,5,-dihydro-oxazol-2-yl)-quinazoline-4,6-diamine (Varlitinib, ASLAN001 Example 52 disclosed in WO2005/016346), is a small-molecule pan-HER inhibitor.

Some of the patients who had previously had several lines of therapy which had failed at some stage were given Varlitinib monotherapy showed a surprising level of efficacy. Thus Varlitinib appears to be efficacious and able to overcome both primary and secondary therapy resistance in cancer.

Thus the present inventors believe that a compound of formula (I), in particular Varlitinib, will be useful in the treatment of refractory and/or resistant cancers.

SUMMARY OF THE DISCLOSURE

Thus there is provided a method of treating a refractory and/or resistant cancer in a patient by administering a therapeutically effective amount of a compound of formula (I):

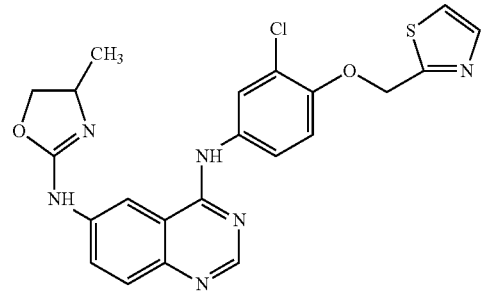 [SMILES: CC1COC(Nc2ccc3ncnc(Nc4ccc(OCc5nccs5)c(Cl)c4)c3c2)=N1]

an enantiomer thereof or a pharmaceutically acceptable salt of any one of the same.

In one embodiment the compound of formula (I) is Varlitinib:

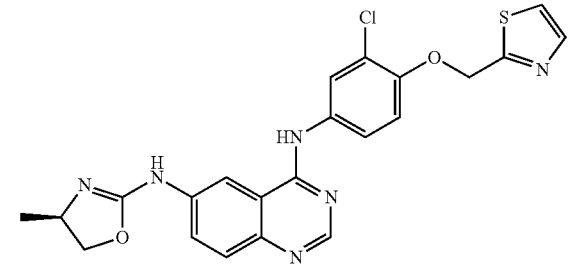 [SMILES: C[C@@H]1COC(Nc2ccc3ncnc(Nc4ccc(OCc5nccs5)c(Cl)c4)c3c2)=N1]

or a pharmaceutically acceptable salt thereof.

In one embodiment the Varlitinib is employed as a free base.

Thus in one aspect there is provided a compound of formula (I) for use in the treatment of a refractory and/or resistant cancer.

In one aspect there provided use of a compound of formula (I) for the manufacture of a medicament for the treatment of refractory and/or resistant cancer.

In one embodiment the cancer is not gastric cancer.

Thus in one aspect the disclosure relates to the treatment of a new patient population where the patients are refractory or resistant to one or more cancer therapies, for example a cancer chemotherapy (cytotoxic chemotherapy).

In one embodiment the cancer is relapsed or recurrent.

In one embodiment the compound of formula (I) is (R)—N4-[3-Chloro-4-(thiazol-2-ylmethoxy)-phenyl]-N6-(4-methyl-4,5,-dihydro-oxazol-2-yl)-quinazoline-4,6-diamine or a pharmaceutically acceptable salt thereof or a pro-drug thereof.

In one embodiment the compound of formula (I) (such as Varlitinib) is administered bi-daily, for example at a dose in the range 100 mg to 900 mg on each occasion, in particular 300 mg, 400 mg or 500 mg each dose.

In one embodiment the cancer therapy according to the present disclosure consists of Varlitinib, for example administered once or twice daily at a dose in the range 100 mg to 500 mg, such as 200 mg, 300 mg or 400 mg.

In some instances patients may benefit from having the initial dose reduced to 300 mg or 200 mg bi-daily.

Other patients may benefit from receiving the compound of formula (I), such as Varlitinib for in a regime which is non-continuous, for example taking medication on alternate days instead of each day or taking medication for four sequential days followed by one, two or three days without medication.

In one embodiment the compound of formula (I) is administered as pharmaceutical formulation comprising one or more pharmaceutically acceptable excipients.

In one embodiment the compound of formula (I) or is formulation comprising the same administered orally, for example as tablet or capsule.

In one embodiment the target patient population is EGFR and/or HER2 positive or are HER2 amplified.

In one embodiment the treatment is adjuvant therapy, for example after surgery or after chemotherapy.

In one embodiment the therapy according to the present disclosure is neo-adjuvant therapy, for example to shrink a tumor before surgery or to increase the efficacy of cytotoxic chemotherapy.

In one embodiment the tumour is a solid tumour. In one embodiment the cancer is a primary cancer, secondary cancer, metastasis or combination thereof. In one embodiment the treatment according to the present disclosure is suitable for the treatment of secondary tumours. In one embodiment the treatment according to the present disclosure is suitable for the treatment of secondary tumours. In one embodiment the cancer is metastatic cancer. In one embodiment the treatment according to the present disclosure is suitable for the treatment of primary cancer and metastases.

In one embodiment the treatment according to the present disclosure is suitable for the treatment of cancerous cell in a lymph node, from a cancer according to the present disclosure.

In one embodiment the patient is a human.

In one embodiment the therapy of the present disclosure is employed an monotherapy.

DETAILED DISCLOSURE

Refractory cancer as employed herein is intended to refer to a cancer that does not respond to one or more cancer treatments, for example does not respond to chemotherapy or a combination of chemotherapeutic agents and/or does not respond to radiotherapy or the like.

Resistance is employed interchangeably herein with refractory, unless the context indicates otherwise.

In one embodiment the resistance is primary resistance.

In one embodiment the resistance is acquired resistance.

Cholangiocarcinoma as referred to herein is a form of cancer that is composed of mutated epithelial cells (or cells showing characteristics of epithelial differentiation) that originate in the bile ducts which drain bile from the liver into the small intestine.

General guidelines for operability include:
Absence of lymph node or liver metastases
Absence of involvement of the portal vein
Absence of direct invasion of adjacent organs
Absence of widespread metastatic disease Monotherapy as employed herein refers to therapy that is targeted at one receptor or receptor family, where the therapy is not employed in combination with cytotoxic chemotherapy. In particular the therapy targets one or more HER receptors. In one embodiment the monotherapy is a pan-HER therapy, for example Varlinitib and/or one or more antibody molecule (including or antibody binding fragments specific) to a HER receptor.

In one embodiment the monotherapy is administered for 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 months or more.

In one embodiment the therapy of the present disclosures employs Varlitinib in combination with a biological therapeutic, such as one or more antibody molecules (including an antibody binding fragment).

In one embodiment the treatment of the present disclosure is neo-adjuvant therapy, for example to shrink the tumour/carcinoma before surgery to remove the cancerous tissue or before chemotherapy, in particular to improve the chances of success of the surgery or to reduce the severity of the treatment required.

In one embodiment the treatment of the present disclosure is adjuvant therapy, for example following surgery to remove the cancerous tissue or following cytotoxic chemotherapy or both.

In patients where not all the cancerous tissue is removed by surgery then the patient may benefit from combination adjuvant therapy comprising a compound of formula (I) and chemotherapy or radiotherapy, prior to receiving monotherapy according to the present disclosure.

Analysis of patients to establish if their cancer is EGFR and HER2 positive is known and is routine in the art. Establishing if a cancer is HER2 amplified is also routine in the art.

Varlitinib at an appropriate dose is capable of inhibiting HER1, HER2 and HER4 directly and thought to be capable of inhibiting HER3 indirectly.

In one embodiment the compound of formula (I) (in particular Varlitinib) at least inhibits the activity of HER1 and HER2, HER1 and HER4 or HER2 and HER4.

In one embodiment the compound of formula (I) (in particular Varlitinib) at least inhibits the activity of HER1, HER2 and HER4, for example directly inhibits the activity of HER1, HER2 and HER4.

In one embodiment the compound of formula (I) (in particular Varlitinib) inhibits the activity of HER1, HER2, HER3 and HER4, for example directly inhibits the activity of HER1, HER2, and HER4, and indirectly inhibits the activity of HER3.

In one embodiment each dose of the compound of formula (I), ((in particular Varlitinib) is in the range 100 to 900 mg, for example each dose is in the range of 300 to 500 mg, such as 400 mg, for example administered once or twice daily, such as twice daily.

In one embodiment the compound of formula (I), such as Varlitinib, is employed with a combination of HER inhibitors, for example a combination of Varlitinib and Herceptin (trastuzumab) and/or pertuzumab. Surprisingly a combination of Varlitinib and Herceptin show more therapeutic activity than either entity alone.

In one embodiment the HER inhibitor is a combination of trastuzumab-emtansine and Varlitinib.

In one embodiment the treatment of the present disclosure is administered for a non-epithelial cancer in which HER inhibition is effective.

In one embodiment the treatment of the present disclosure is administered for epithelial cancer, for example is selected from liver cancer, biliary tract cancer, breast cancer (such as none ER+ breast cancer), prostate cancer, colorectal cancer, ovarian cancer, cervical cancer, lung cancer, gastric cancer, pancreatic, bone cancer, bladder cancer, head and neck cancer, thyroid cancer, skin cancer, renal cancer, and oesophagus cancer, for example gastric cancer, hepatocellular carcinoma and cholangiocarcinoma.

In one embodiment the cancer is selected from the group comprising hepatocellular carcinoma, cholangiocarcinoma, breast cancer, prostate cancer, colorectal cancer, ovarian cancer, lung cancer, gastric cancer, pancreatic and oesophagus cancer.

In one embodiment the biliary duct cancer is in a location selected from intrahepatic bile ducts, left hepatic duct, right hepatic duct, common hepatic duct, cystic duct, common bile duct, Ampulla of Vater and combinations thereof.

In one embodiment the biliary duct cancer is in an intrahepatic bile duct.

In one embodiment the biliary duct cancer is in a left hepatic duct.

In one embodiment the biliary duct cancer is in a right hepatic duct.

In one embodiment the biliary duct cancer is in a common hepatic duct.

In one embodiment the biliary duct cancer is in a cystic duct.

In one embodiment the biliary duct cancer is in a common bile duct.

In one embodiment the biliary duct cancer is in an Ampulla of Vater.

In one embodiment the epithelial cancer is a carcinoma.

In one embodiment the epithelial cancer is a carcinoma.

In one embodiment the treatment is adjuvant therapy, for example after surgery.

In one embodiment the tumour is a solid tumour. In one embodiment the cancer is a primary cancer, secondary cancer, metastasis or combination thereof. In one embodiment the treatment according to the present disclosure is suitable for the treatment of primary tumours. In one embodiment the treatment according to the present disclosure is suitable for the treatment of secondary tumours. In one embodiment the cancer is metastatic cancer. In one embodiment the treatment according to the present disclosure is suitable for the treatment of primary cancer and metastases. In one embodiment the treatment according to the present disclosure is suitable for the treatment of secondary cancer and metastases. In one embodiment the treatment according to the present disclosure is suitable for the treatment of primary cancer, secondary cancer and metastases.

In one embodiment the treatment according to the present disclosure is suitable for the treatment of cancerous cells in a lymph node, from a cancer according to the present disclosure.

In one embodiment the liver cancer is primary liver cancer. In one embodiment the liver cancer is secondary liver cancer. In one embodiment the liver cancer is stage 1, 2, 3A, 3B, 3C, 4A or 4B.

In one embodiment the gastric cancer is stage 0, I, II, III or IV.

In one embodiment the patient is a human.

Cancers

Liver cancer as employed herein refers to cancer of the liver, for example hepatocellular carcinoma including fibrolamellar carcinoma, cholangiocarcinoma, angiosarcoma and hepatoblastoma.

Gastric cancer as employed herein refers to cancer of the stomach, for example squamous cell cancers, lymphoma including non-hodgkin lymphoma, gastrointestinal stromal tumour, or neuroendocrine tumours.

Prostate cancer as employed herein refers to cancer of the prostate, for example ductal adenocarcinoma, transitional cell (urothelial cancer), squamous cell cancer, carcinoid of the prostate, small cell cancer or sarcoma and sarcomatoid cancer.

Pancreatic cancer as employed herein includes exocrine cancers (including rare forms thereof such as cystitic tumours, and cancer of the acinar cells), endocrine pancreatic tumours (including gastrinomas, insulinomas, somatostatinomas, VIPomas, glucagonomas), pancreatoblastoma, sarcomas of the pancreas and lymphoma.

Biliary tract cancer as employed herein refers to cholangiocarcinoma (intrahepatic, extrahepatic), gall bladder cancer and ampullary carcinoma.

Colorectal cancer as employed herein refers to cancer or the colon and/or rectum and includes squamous cell cancers, carcinoid tumours, sarcomas and lymphomas.

Breast cancer as employed herein refers to cancer of the breast and includes ductal cardinoma in situ, lobular carcinoma in situ, invasive ductal breast cancer, invasive lobular breast cancer, invasive breast cancer, Paget's disease, angiosarcoma of the breast and rare types of breast cancer such as medullary breast cancer, mucinous breast cancer, tubular breast cancer, adenoid cystic carcinoma of the breast metaplastic breast cancer, basal type breast cancer and papillary breast cancer.

Ovarian cancer as employed herein refers to cancer of an ovary and includes serious, endometrioid, clear cell, mucinous, undifferentiated or unclassified, germline and other rare ovarian tumours such as teratoma of the ovary (mature teratoma and immature teratoma) and borderline ovarian tumours. Epithelia ovarian cancers are serious, endometrioid, clear cell, mucinous and undifferentiated or unclassified.

There are more than 30 different types of ovarian cancer which are classified according to the type of cell from which they start. Cancerous ovarian tumours can start from three common cell types:

Surface Epithelium—cells covering the lining of the ovaries,

Germ Cells—cells that are destined to form eggs, and

Stromal Cells—Cells that release hormones and connect the different structures of the ovaries.

The present disclosure relates to treatment of ovarian cancer from any source, for example as described herein, in particular epithelium cells. Epithelial ovarian carcinomas (EOCs) account for 85 to 90 percent of all cancers of the ovaries.

Common Epithelial Tumours—

Epithelial ovarian tumours develop from the cells that cover the outer surface of the ovary. Most epithelial ovarian tumours are benign (noncancerous). There are several types of benign epithelial tumours, including serous adenomas, mucinous adenomas, and Brenner tumours. Cancerous epithelial tumours are carcinomas—meaning they begin in the tissue that lines the ovaries. These are the most common and most dangerous of all types of ovarian cancers. Unfortunately, almost 70 percent of women with the common epithelial ovarian cancer are not diagnosed until the disease is advanced in stage.

There are some ovarian epithelial tumours whose appearance under the microscope does not clearly identify them as cancerous. These are called borderline tumours or tumours of low malignant potential (LMP tumours). The method of the present disclosure includes treatment of the latter.

Germ Cell Tumours—

Ovarian germ cell tumours develop from the cells that produce the ova or eggs. Most germ cell tumours are benign (non-cancerous), although some are cancerous and may be life threatening. The most common germ cell malignancies are maturing teratomas, dysgerminomas, and endodermal sinus tumours. Germ cell malignancies occur most often in teenagers and women in their twenties. Today, 90 percent of patients with ovarian germ cell malignancies can be cured and their fertility preserved.

Stromal Tumours—

Ovarian stromal tumours are a rare class of tumours that develop from connective tissue cells that hold the ovary together and those that produce the female hormones, estrogen and progesterone. The most common types are granulosa-theca tumours and Sertoli-Leydig cell tumours. These tumours are quite rare and are usually considered low-grade cancers, with approximately 70 percent presenting as Stage I disease (cancer is limited to one or both ovaries).

Primary Peritoneal Carcinoma—

The removal of one's ovaries eliminates the risk for ovarian cancer, but not the risk for a less common cancer called Primary Peritoneal Carcinoma. Primary Peritoneal Carcinoma is closely rated to epithelial ovarian cancer (most common type). It develops in cells from the peritoneum (abdominal lining) and looks the same under a microscope. It is similar in symptoms, spread and treatment.

Stages of Ovarian Cancer

Once diagnosed with ovarian cancer, the stage of a tumour can be determined during surgery, when the doctor can tell if the cancer has spread outside the ovaries. There are four stages of ovarian cancer—Stage I (early disease) to Stage IV (advanced disease). The treatment plan and prognosis (the probable course and outcome of your disease) will be determined by the stage of cancer you have.

Following is a description of the various stages of ovarian cancer:

Stage I—Growth of the cancer is limited to the ovary or ovaries.

Stage IA—Growth is limited to one ovary and the tumour is confined to the inside of the ovary. There is no cancer on the outer surface of the ovary. There are no ascites present containing malignant cells. The capsule is intact.

Stage IB—Growth is limited to both ovaries without any tumour on their outer surfaces. There are no ascites present containing malignant cells. The capsule is intact.

Stage IC—The tumour is classified as either Stage IA or IB and one or more of the following are present: (1) tumour is present on the outer surface of one or both ovaries; (2) the capsule has ruptured; and (3) there are ascites containing malignant cells or with positive peritoneal washings.

Stage II—Growth of the cancer involves one or both ovaries with pelvic extension.

Stage IIA—The cancer has extended to and/or involves the uterus or the fallopian tubes, or both.

Stage IIB—The cancer has extended to other pelvic organs.

Stage IIC—The tumour is classified as either Stage IIA or IIB and one or more of the following are present: (1) tumour is present on the outer surface of one or both ovaries; (2) the capsule has ruptured; and (3) there are ascites containing malignant cells or with positive peritoneal washings.

Stage III—Growth of the cancer involves one or both ovaries, and one or both of the following are present: (1) the cancer has spread beyond the pelvis to the lining of the abdomen; and (2) the cancer has spread to lymph nodes. The tumour is limited to the true pelvis but with histologically proven malignant extension to the small bowel or omentum.

Stage IIIA—During the staging operation, the practitioner can see cancer involving one or both of the ovaries, but no cancer is grossly visible in the abdomen and it has not spread to lymph nodes. However, when biopsies are checked under a microscope, very small deposits of cancer are found in the abdominal peritoneal surfaces.

Stage IIIB—The tumour is in one or both ovaries, and deposits of cancer are present in the abdomen that are large enough for the surgeon to see but not exceeding 2 cm in diameter. The cancer has not spread to the lymph nodes.

Stage IIIC—The tumour is in one or both ovaries, and one or both of the following is present: (1) the cancer has spread to lymph nodes; and/or (2) the deposits of cancer exceed 2 cm in diameter and are found in the abdomen.

Stage IV—This is the most advanced stage of ovarian cancer. Growth of the cancer involves one or both ovaries and distant metastases (spread of the cancer to organs located outside of the peritoneal cavity) have occurred. Finding ovarian cancer cells in pleural fluid (from the cavity which surrounds the lungs) is also evidence of stage IV disease.

In one embodiment the ovarian cancer is: type I, for example IA, IB or IC; type II, for example IIA, IIB or IIC; type III, for example IIIA, IIIB or IIIC; or type IV.

The present disclosure relates to treatment of any stage of ovarian cancer, in particular as described herein.

Lung cancers are classified according to histological type and are categorized by the size and appearance of the malignant cells seen by a histopathologist under a microscope. For therapeutic purpose, two broad classes are distinguished: non-small cell lung carcinoma and small cell lung carcinoma.

In one embodiment the epithelial cancer is lung cancer, for example small-cell lung cancer (SCLC) and non-small-cell lung cancer (NSCLC).

Non-Small-Cell Lung Carcinoma—

The three main subtypes of NSCLC are adenocarcinoma, squamous-cell carcinoma and large-cell carcinoma.

Nearly 40% of lung cancers are adenocarcinoma, which usually originates in peripheral lung tissue. A subtype of adenocarcinoma, the bronchioloalveolar carcinoma, is more common in female never-smokers, and may have a better long term survival.

Squamous-cell carcinoma accounts for about 30% of lung cancers. They typically occur close to large airways. A hollow cavity and associated cell death are commonly found at the center of the tumour. About 9% of lung cancers are large-cell carcinoma. These are so named because the cancer cells are large, with excess cytoplasm, large nuclei and conspicuous nucleoli.

Small-Cell Lung Carcinoma—

In small-cell lung carcinoma (SCLC), the cells contain dense neurosecretory granules (vesicles containing neuroendocrine hormones), which give this tumour an endocrine/paraneoplastic syndrome association. Most cases arise in the larger airways (primary and secondary bronchi). These cancers grow quickly and spread early in the course of the disease. Sixty to seventy percent have metastatic disease at presentation.

In one embodiment the cancer is non-small lung carcinoma.

In one embodiment there is provided treatment of renal cancer, for example renal cell carcinoma and/or urothelial cell carcinoma using an oncolytic adenovirus as disclosed herein. Other examples of renal cancer include squamous cell carcinoma, juxtaglomerular cell tumour (reninoma), angiomyolipoma, renal oncocytoma, Bellini duct carcinoma, clear-cell sarcoma of the kidney, mesoblastic nephroma, Wilms' tumour, mixed epithelial stromal tumour, clear cell adenocarcinoma, transitional cell carcinoma, inverted papilloma, renal lymphoma, teratoma, carcinosarcoma, and carcinoid tumour of the renal pelvis.

In one embodiment the cancer is bladder cancer, for example is any of several types of malignancy arising from the epithelial lining (i.e., the urothelium) of the urinary bladder. About 90% of bladder cancers are transitional cell carcinoma. The other 10% are squamous cell carcinoma, adenocarcinoma, sarcoma, small cell carcinoma, and secondary deposits from cancers elsewhere in the body. The staging of is given below.

T (Primary Tumour)
    TX Primary tumour cannot be assessed
    T0 No evidence of primary tumour
    Ta Non-invasive papillary carcinoma
    Tis Carcinoma in situ ('flat tumour')
    T1 Tumour invades subepithelial connective tissue
    T2a Tumour invades superficial muscle (inner half)
    T2b Tumour invades deep muscle (outer half)
    T3 Tumour invades perivesical tissue:
    T3a Microscopically
    T3b Macroscopically (extravesical mass)
    T4a Tumour invades prostate, uterus or vagina
    T4b Tumour invades pelvic wall or abdominal wall N (Lymph Nodes)
    NX Regional lymph nodes cannot be assessed
    N0 No regional lymph node metastasis
    N1 Metastasis in a single lymph node 2 cm or less in greatest dimension
    N2 Metastasis in a single lymph node more than 2 cm but not more than 5 cm in greatest dimension, or multiple lymph nodes, none more than 5 cm in greatest dimension
    N3 Metastasis in a lymph node more than 5 cm in greatest dimension M (Distant Metastasis)
    MX Distant metastasis cannot be assessed
    M0 No distant metastasis
    M1 Distant metastasis.

Thyroid cancer as employed herein refers to cancer of the thyroid originating from follicular or parafollicular thyroid cells and includes papillary thyroid cancer (75% to 85% of cases); follicular thyroid cancer (10% to 20% of cases); medullary thyroid cancer (5% to 8% of cases)—cancer of the parafollicular cells, often part of multiple endocrine neoplasia type 2; poorly differentiated thyroid cancer; anaplastic thyroid cancer (less than 5% of cases) is not responsive to treatment and can cause pressure symptoms, thyroid lymphoma, squamous cell thyroid carcinoma, sarcoma of thyroid.

Renal cancer as employed herein refers to cancer of the kidney, for example renal cell carcinoma and transitional cell carcinoma of the renal pelvis, such as squamous cell carcinoma, juxtaglomerular cell tumor (reninoma), angiomyolipoma, renal oncocytoma, bellini duct carcinoma, clear-cell sarcoma of the kidney, mesoblastic nephroma, Wilms' tumor, mixed epithelial stromal tumor, clear cell adenocarcinoma, transitional cell carcinoma, inverted papilloma, renal lymphoma, teratoma, carcinosarcoma; carcinoid tumor of the renal pelvis.

Bladder cancer as employed herein refers to cancer of the bladder including transitional cell bladder cancer, carcinoma in situ, papillary cancer and rarer types of bladder cancer such as squamous cell cancer and adenocarcinoma.

Esophageal cancer as employed herein refers to cancer of the esophagus including esophageal squamous-cell carcinomas, esophageal adenocarcinomas, and variants of squamous-cell carcinoma, and non-epithelial tumors, such as leiomyosarcoma, malignant melanoma, rhabdomyosarcoma, lymphoma, among others.

Head and neck cancer as employed herein refers to cancer of the neck and/or head, including mouth cancer, nasopharyngeal cancer, oropharyngeal cancer, paranasal sinus cancer and salivary gland cancer.

Chemotherapeutic Agents

Chemotherapeutic agent and chemotherapy or cytotoxic agent are employed interchangeably herein unless the context indicates otherwise.

Chemotherapy as employed herein is intended to refer to specific antineoplastic chemical agents or drugs that are "selectively" destructive to malignant cells and tissues, for example alkylating agents, antimetabolites including thymidylate synthase inhibitors, anthracyclines, anti-microtubule agents including plant alkaloids, topoisomerase inhibitors, parp inhibitors and other antitumour agents. Selectively in this context is used loosely because of course many of these agents have serious side effects.

Examples of alkylating agents, which may be employed in the method of the present disclosure include an alkylating agent nitrogen mustards, nitrosoureas, tetrazines, aziridines, platins and derivatives, and non-classical alkylating agents.

Example a platinum containing chemotherapeutic agent (also referred to as platins), such as cisplatin, carboplatin, oxaliplatin, satraplatin, picoplatin, nedaplatin, triplatin and lipoplatin (a liposomal version of cisplatin), in particular cisplatin, carboplatin and oxaliplatin.

Nitrogen mustards include mechlorethamine, cyclophosphamide, melphalan, chlorambucil, ifosfamide and busulfan.

Nitrosoureas include N-Nitroso-N-methylurea (MNU), carmustine (BCNU), lomustine (CCNU) and semustine (MeCCNU), fotemustine and streptozotocin. Tetrazines include dacarbazine, mitozolomide and temozolomide.

Aziridines include thiotepa, mytomycin and diaziquone (AZQ).

Examples of antimetabolites, which may be employed in the method of the present disclosure, include anti-folates (for example methotrexate and pemetrexed), purine analogues (for example thiopurines, such as azathiopurine, mercaptopurine, thiopurine, fludarabine (including the phosphate form), pentostatin and cladribine), pyrimidine analogues (for example fluoropyrimidines, such as 5-fluorouracil and prodrugs thereof such as capecitabine [Xeloda®]), floxuridine, gemcitabine, cytarabine, decitabine, raltitrexed(tomudex) hydrochloride, cladribine and 6-azauracil.

Examples of anthracyclines, which may be employed in the method of the present disclosure, include daunorubicin (Daunomycin), daunorubicin (liposomal), doxorubicin (Adriamycin), doxorubicin (liposomal), epirubicin, idarubicin, valrubicin currenity used only to treat bladder cancer and mitoxantrone an anthracycline analog, in particular doxorubicin.

Examples of anti-microtubule agents, include include vinca alkaloids and taxanes.

Vinca alkaloids include completely natural chemicals for example vincristine and vinblastine and also semi-synthetic vinca alkaloids, for example vinorelbine, vindesine, and vinflunine.

Taxanes include paclitaxel, docetaxel and abraxane and derivatives of thereof. Derivatives of taxanes as employed herein includes reformulations of taxanes like taxol, for example in a micelluar formulaitons, derivatives also include chemical derivatives wherein synthetic chemistry is employed to modify a starting material which is a taxane.

Topoisomerase inhibitors, which may be employed in a method of the present disclosure include type I topoisomerase inhibitors, type II topoisomerase inhibitors and type II topoisomerase poisons. Type I inhibitors include topotecan, irinotecan, indotecan and indimitecan. Type II inhibitors include genistein and ICRF 193 which has the following structure:

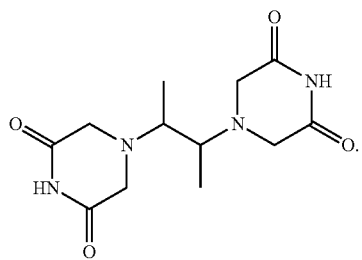 [SMILES: CC(C(C)N1CC(=O)NC(=O)C1)N1CC(=O)NC(=O)C1]

Type II poisons include amsacrine, etoposide, etoposide phosphate, teniposide and doxorubicin and fluoroquinolones.

Non-Chemotherapy Combination Therapies

In one embodiment the therapy according to the present disclosure is employed in combination with a further cancer therapy, wherein the further cancer therapy is not a cytotoxic chemotherapy. In one aspect the further cancer therapy is cancer immunotherapy, for example an antibody molecule, a cytokine, a cellular therapy and/or an oncolytic virus.

In one embodiment the cancer immunotherapy comprises a check-point inhibitor, for example one or more selected from the group comprising a CTLA-4 inhibitor, a PD-1 inhibitor, a PD-L1 inhibitor, in particular an antibody or binding fragment thereof.

In one embodiment the cancer immunotherapy is alemtuzumab, ipilimumab, nivolumab, ofatumumab and rituximab.

In one embodiment the further cancer therapy comprises ganciclovir, which may assist in controlling immune responses and/or tumour vasculation.

In one embodiment the further cancer therapy includes a PARP inhibitor.

In one embodiment the combination therapy according to the present disclosure comprises a RON inhibitor, for example as disclosed WO2008/058229, incorporated herein by reference.

In one embodiment the further cancer therapy includes an inhibitor of cancer metabolism with specific inhibition of the activity of the DHODH enzyme.

Examples of pharmaceutically acceptable salts include but are not limited to acid addition salts of strong mineral acids such as HCl and HBr salts and addition salts of strong organic acids, such as a methansulfonic acid salt, tosylates, furoates and the like, including di, tri salts thereof, such as ditosylates.

"Comprising" in the context of the present specification is intended to meaning including. Where technically appropriate, embodiments of the invention may be combined. Embodiments are described herein as comprising certain features/elements. The disclosure also extends to separate embodiments consisting or consisting essentially of said features/elements.

Technical references such as patents and applications are incorporated herein by reference.

Any embodiments specifically and explicitly recited herein may form the basis of a disclaimer either alone or in combination with one or more further embodiments.

SUMMARY OF THE FIGURES

FIG. 1 shows a patient's response to Varlitinib 400 mg bi-daily as a Monotherapy FIG. 2 shows the patient response for Example 2

EXAMPLES

Example 1 Varlitinib 400 mg Bi-Daily Monotherapy

A 45 year-old male stage IV cholangiocarcinoma EGFR positive (3+) cancer patient had progressive disease following:
  first line treatment with gemcitabine (partial remission), and
  second line treatment with cisplatin and 5-FU.
The results are shown in FIG. 1. After treatment cycle 6 with Varlitinib 400 mg bi-daily the liver tumours decreased in size up to 23% and the tumour marker CA 19-9 fell from ~900 U/ml to ~250 U/ml.

Example 2 Varlitinib 400 mg Bi-Daily Combination Therapy

A 58 year-old, male, stage IV, extra-hepatic cholangiocarcinoma, prior treatment:
  Whipple
  Radiotherapy
  Gemzar/cisplatin for 6 months
For the first 6 cycles, the patient received Varlitinib 400 mg BID continuously with cisplatin (80 mg/m$^2$ every 3 weeks) and capecitabine (1000 mg/m2 BID, 2 weeks on, 1 week off). Image scan at the end of cycle 6 showed 85.77% reduction in tumour size. After cycle 6, the patient received varlitinib monotherapy and tumor scan at the end of cycle 8 showed 87% reduction. This patient showed partial remission for 24 weeks. However, at the end of cycle 10, image scan showed tumour enlarged to the extent that met criteria for disease progression based on RECIST (>20% increase against nadir), so the patient was withdrawn from this study. In summary, the patient received varlitinib with chemo for 6 cycles and varlitinib monotherapy for another 4 cycles (3 weeks per cycle).

Example 3 Treatment of Stage IV Intrahepatic Cholangiocarcinoma with Varlitinib 400 mg Bi-Daily Orally and FOLFOX A 51 year-old female who had a medical history of meningioma post excision with left craniotomy was diagnosed with intrahepatic cholangiocarcinoma, stage IV with metastasis to portacaval lymph nodes and liver in August 2014. She received left hemihepatectomy followed by 6 cycles of adjuvant gemcitabine and cisplatin. The patient's disease progressed in May 2015 and she received 1st line gemcitabine and cisplatin in metastatic setting, to which he did not respond. After disease progression on gemcitabine and cisplatin, she was enrolled into the ASLAN001-002SG study in August 2015 and received Varlitinib 400 mg BID in combination with mFOLFOX6 (2 weeks per cycle). To date (22 Aug. 2016), the patient has completed 9 cycles of Varlitinib and mFOLFOX6, as well as, 9 cycles of varlitinib monotherapy and the latest tumor assessment completed after cycle 18 continues to show partial response with 53% reduction in tumor size as the best response from baseline.

The invention claimed is:

1. A method of treating a human patient with refractory or resistant biliary tract cancer, comprising administering to said patient a therapeutically effective amount of a compound of formula (I):

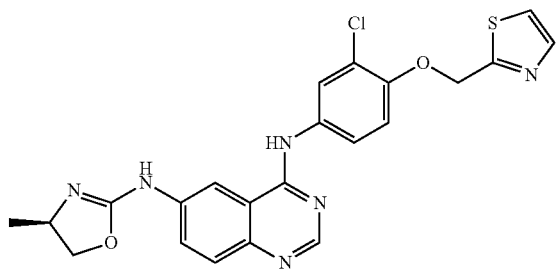 [SMILES: C[C@@H]1COC(Nc2ccc3ncnc(Nc4ccc(OCc5nccs5)c(Cl)c4)c3c2)=N1]

or a pharmaceutically acceptable salt thereof, wherein each dose of the compound of formula (I) is in the range 100 to 900 mg; and wherein the compound of formula (I) or pharmaceutically acceptable salt thereof is employed as a monotherapy or as part of a combination therapy that does not comprise a cytotoxic chemotherapy.

2. A method according to claim 1, wherein the compound of formula (I) is provided as the free base.

3. A method according to claim 1, wherein the compound of formula (I) is administered as a pharmaceutical formulation.

4. A method according to claim 1, wherein the compound of formula (I) or a pharmaceutical formulation comprising same is administered orally.

5. A method according to claim 1, wherein the compound of formula (I) or a pharmaceutical formulation comprising the same is administered bi-daily.

6. A method according to claim 1, wherein each dose of the compound of formula (I) is in the range 100 to 500 mg.

7. A method according to claim 6, wherein each dose of the compound of formula (I) is in the range 300 to 500 mg.

8. A method according to claim 7 wherein each dose is 400 mg.

9. A method according to claim 1, wherein the compound of formula (I) or formulation comprising the same is employed as a monotherapy.

10. A method according to claim 1, wherein the therapy is part of a combination therapy.

11. A method according to claim 1, wherein the therapy is an adjuvant therapy.

12. A method according to claim 1, wherein the biliary tract cancer is cholangiocarcinoma.

13. A method according to claim 12, wherein the cholangiocarcinoma is in an intrahepatic bile duct.

14. A method according to claim 1, wherein the biliary tract cancer is gall bladder cancer.

* * * * *